United States Patent [19]
Chaisson et al.

[11] Patent Number: 5,665,116
[45] Date of Patent: Sep. 9, 1997

[54] METHOD AND APPARATUS FOR CATHETERIZATION TO DILATE VASCULAR BLOCKAGE

[76] Inventors: Gary A. Chaisson, 215 Angelle Ct.; Craig M. Walker, 312 Keystone Loop, both of Houma, La. 70360

[21] Appl. No.: 555,919

[22] Filed: Nov. 13, 1995

[51] Int. Cl.⁶ ............................................. A61F 2/06
[52] U.S. Cl. ............................ 623/1; 623/12; 606/194
[58] Field of Search ........................... 623/1, 11, 12; 606/151, 153, 191, 192, 194, 195

[56] References Cited

U.S. PATENT DOCUMENTS

| | | | |
|---|---|---|---|
| 4,649,922 | 3/1987 | Wiktor | 606/195 |
| 4,733,665 | 3/1988 | Palmaz | 128/343 |
| 4,877,030 | 10/1989 | Beck et al. | 623/1 |
| 5,049,131 | 9/1991 | Deuss | 604/96 |
| 5,066,298 | 11/1991 | Hess | 606/194 |
| 5,100,381 | 3/1992 | Burns | 604/96 |
| 5,102,417 | 4/1992 | Palmaz | 606/195 |
| 5,135,536 | 8/1992 | Hillstead | 606/195 |
| 5,441,515 | 8/1995 | Khosravi et al. | 623/1 |

*Primary Examiner*—Randy C. Shay
*Attorney, Agent, or Firm*—Pravel, Hewitt, Kimball & Krieger

[57] ABSTRACT

An method for implanting a coiled prosthesis within a body passageway having a longitudinally extending central axis first places a coiled prosthesis upon a catheter in a coiled, smaller diameter configuration. The prosthesis and catheter are inserted into the body passageway by catheterization of the body passageway. The prosthesis is expanded in order to unwind the coiled ring prosthesis to a larger diameter configuration that has a diameter larger than the smaller diameter configuration of the prosthesis initially. The prosthesis forms an annular ring having spaced apart first and second annular surfaces. The body passageway is supported in a direction away from the annular ring and along the passageway wall with multiple, longitudinally extending strut support members that each extend away from the ring, and each of which extends partially circumferentially around the passageway. After the prosthesis has been expanded, the catheter is withdrawn from the body passageway.

8 Claims, 4 Drawing Sheets

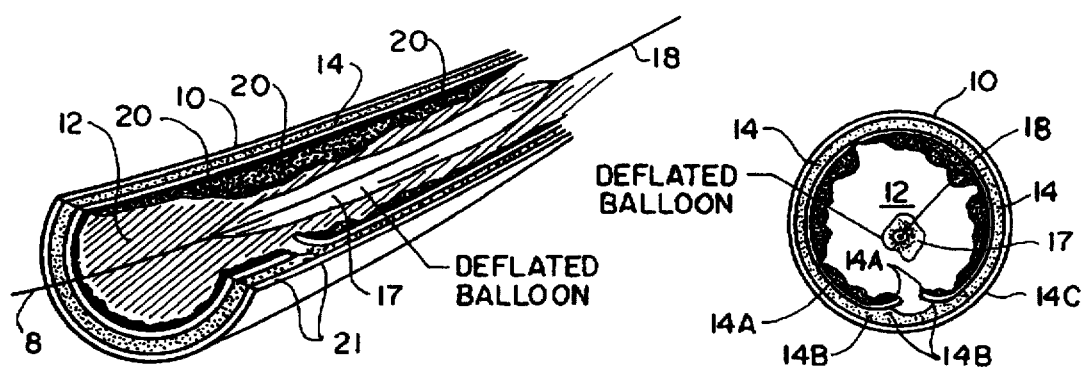
FIG. 4A    FIG. 4B
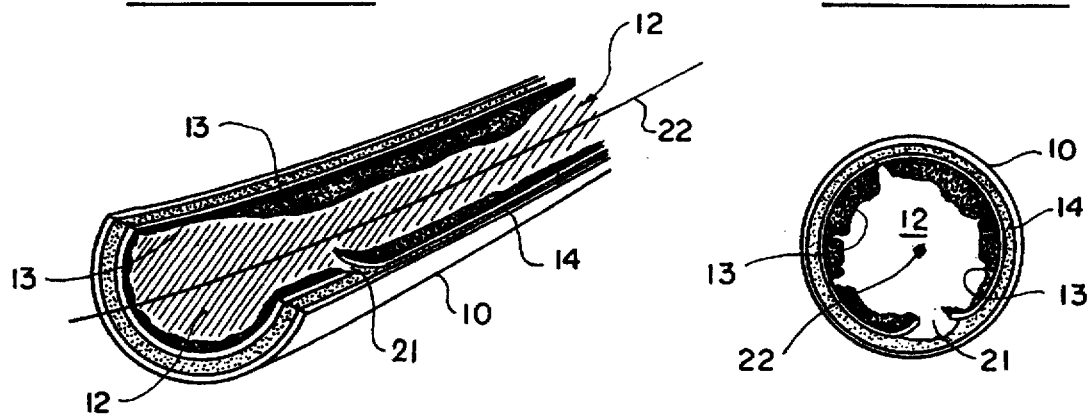
FIG. 5    FIG. 6
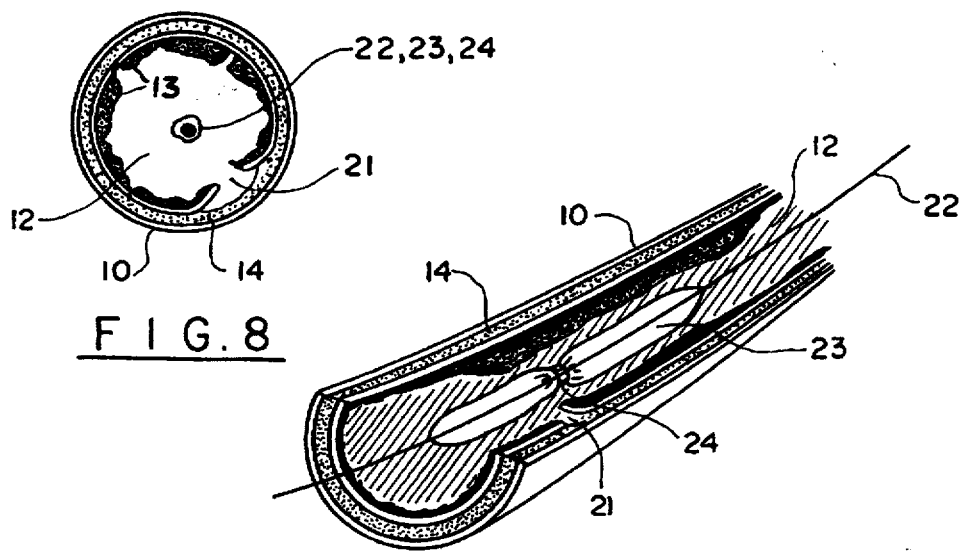
FIG. 8
FIG. 7

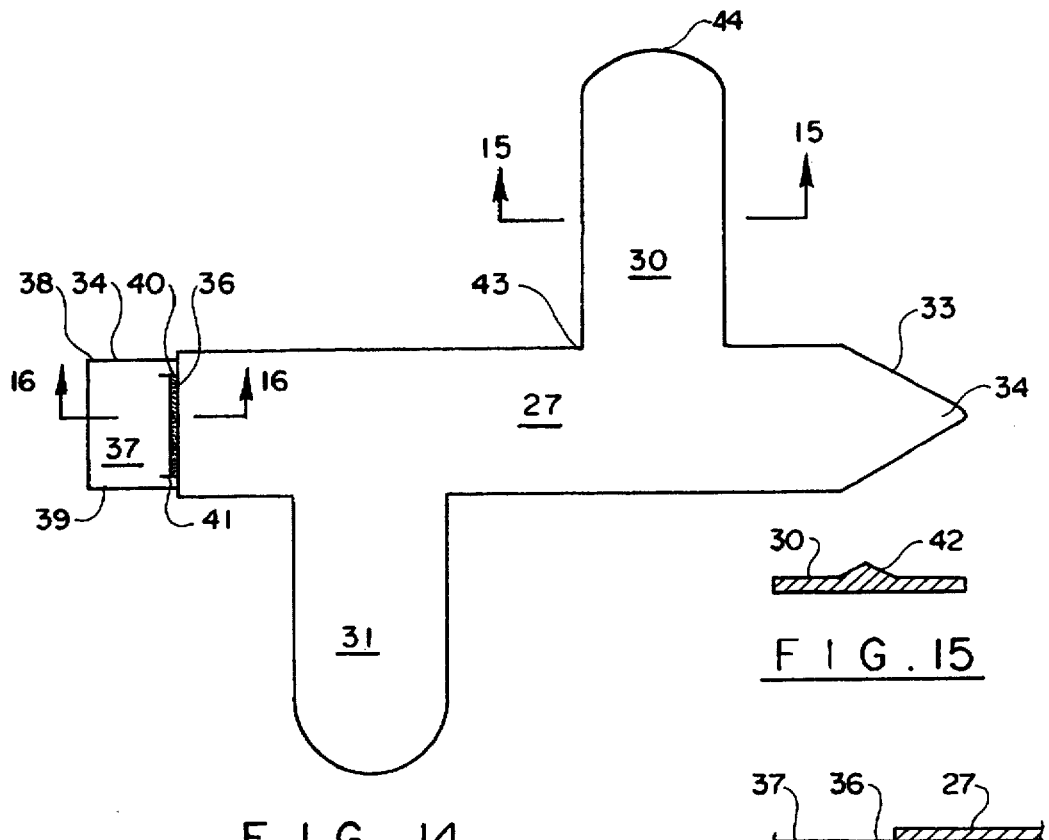
FIG. 14
FIG. 15
FIG. 16
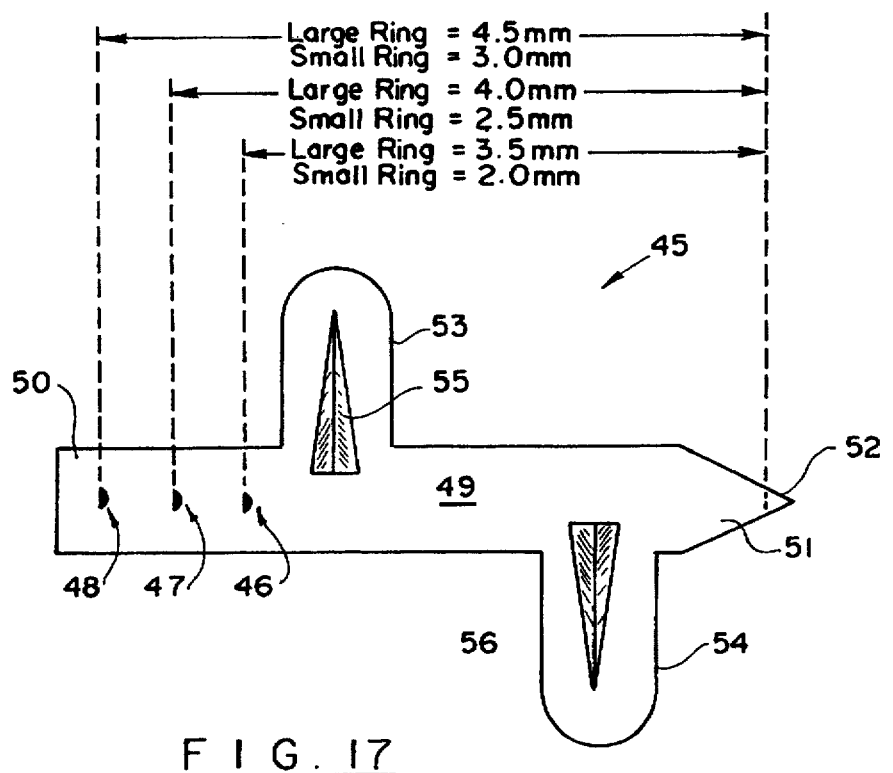
FIG. 17

METHOD AND APPARATUS FOR CATHETERIZATION TO DILATE VASCULAR BLOCKAGE

BACKGROUND OF THE INVENTION

1. Field of the Invention

The present invention relates to the treatment of coronary artery disease by mechanical dilation of blockages in the coronary arteries. More particularly, the present invention relates to a method and apparatus for dilating blockage in coronary arteries wherein a catheter assembly carries a balloon to the blockage site in a patient's artery, and the balloon is expanded to uncoil a coiled ring structure having longitudinally extended struts is carried upon the balloon, and which locks to remain in an uncoiled position, holding the blockage, flap or dissection in open dilated position.

2. General Background

A common medical condition that threatens thousands of lives is caused by blockage of the coronary arteries. Medical procedures have been designed to remove the blockage in many cases so that increased blood flow travels through the previously diseased artery. Restenosis means that coronary artery blockage returns. It is though that restenosis is due to tissue growing in the inner lining of the artery as it heals. Approximately 30% of the patients undergoing PTCA will experience restenosis. Several procedures have been developed in hopes of reducing the restenosis rate. Atherectomy is a technique by which the blockage is actually removed. It is often times referred to as the roto-rooter. This technique initially demonstrated promise but it seems that it does not effect restenosis. Another technique is stent implantation. A stent is a device that is deployed in the vessel to pin back flaps and prevent elastic recoil. Early data suggest that this procedure may reduce stenosis.

The other problem with PTCA is acute occlusion. Occlusion occurs when the artery closes off completely following balloon dilatation. This problem is usually the result of one of two things. A clot can form at the PTCA site and obstruct the vessel, or a dissection can form which is basically a flap made up of the inner and middle layers of the artery. Severe dissections have been treated by long balloon inflation times in hopes of pinning up the flap, by atherectomy where by you go in and cut off the flap, and by stenting which pins up the flap mechanically.

There are several stents currently being researched in the coronary and peripheral circulation, the most well known is the Palmaz stent. It is a stainless steel tube that is prepared by cutting a series of slots in it. It is then placed on a balloon. When the balloon is inflated the tube expends to the diameter of the balloon and foreshortens the stent upon expansion.

Another stent is the Schneider or Wall stent. This is a self-expanding stent. It is similar in design to a Chinese finger cuff. When elongated its diameter is smaller. When allowed to shorten along its longitural axis its diameter increases. Following deployment in a blood vessel it is further expanded with a balloon. Various patents have issued for stents and for catheter arrangements that are directed to the problem of coronary blockage and restenosis.

U.S. Pat. No. 4,733,665, entitled "Expandable Intraluminal Graft, And Method And Apparatus For Implanting An Expandable Intraluminal Graft," issued to Julio C. Palmaz, discloses a graft that is expanded within a blood vessel by an angioplasty balloon associated with a catheter to dilate and expand the lumen of a blood vessel. The graft may be made of a wire mesh tube.

U.S. Pat. No. 5,049,131, entitled "Balloon Catheter," issued to Jacobus A. C. Deuss, discloses a balloon catheter for the widening of passages in the body, such as blood vessels. The apparatus comprises a tubular body connected at one side to the interior of a cylindrical balloon and at another side to a pump unit. The balloon can be enlarged from a first predetermined diameter to a second predetermined diameter without completely withdrawing the catheter from the body passages.

U.S. Pat. No. 5,066,298, entitled "Article And Method Of Sheathing Angioplasty Balloons," issued to Robert L. Hess, discloses a pre-compressed angioplasty balloon catheter and method of manufacture wherein the balloon portion of the catheter is wrapped for storage and for minimizing its outside diameter for purpose of insertion into the body.

U.S. Pat. No. 5,100,381, entitled "Angioplasty Catheter," issued to Matthew M. Burns, discloses an over-the-wire balloon for use in angioplasty and includes a dual lumen shaft formed by a multisection outer tube and multisection inner tube. The outer tube includes a first thin wall outer tube section which is connected to a manifold at its proximal end. The outer tube also includes a second outer tube section which is attached to the distal end of the first outer tube section and which has a greater flexibility. The inner tube has a first thin wall inner tube section which extends generally coaxially through the first outer tube section and into the interior of the second outer tube section. The inner tube also includes a second thin wall inner tube section which is attached to the distal end of the first inner tube section and extends distally beyond the distal end of the outer tube. A balloon is attached to the distal ends of the outer and inner tubes. The inner tube sections have a coating of a low friction material, such as polyimide-polytetrafluoroethylene composite, on their inner walls to facilitate movement of a guide wire through the guide wire lumen of the inner tube.

U.S. Pat. No. 5,100,429, entitled "Endovascular Stent And Delivery System," issued to Edward L. Sinofsky et al., discloses an uncured or partially cured, collagen-based material that is delivered to a selected site in a blood vessel and is crosslinked in the blood vessel by laser energy or other suitable energy to form an endovascular stent. The collagen-based material can be delivered to the blood vessel as a coating on an inflatable balloon mounted on the distal end of a catheter. The collagen-based material can also be delivered to the blood vessel in liquid form and forced through a porous balloon to form a tubular configuration. The collagen-based material is preferably crosslinked by laser radiation carried through an optical fiber to a diffusing tip located within the balloon. In another embodiment, an endovascular stent is formed by rolling a flexible sheet of biologically-compatible material onto a an outside surface of an inflatable balloon. A crosslinkable collagen-based adhesive is used to adhere overlapping portions of the sheet together in the blood vessel and can be used to attach the stent to an inside surface of the blood vessel. The collagen-based adhesive is crosslinked in the blood vessel by application of laser energy or other suitable energy. A photodegradable adhesive can be used on an inside surface of the stent to releasably attach the stent to the inflatable balloon.

U.S. Pat. No. 5,102,417, entitled "Expandable Intraluminal Graft, And Method And Apparatus For Implanting An Expandable Intraluminal Graft," issued to Julio C. Palmaz, discloses a plurality of expandable and deformable intraluminal vascular grafts that are expanded within a blood vessel by an angioplasty balloon associated with a catheter to dilate and expand the lumen of a blood vessel. The grafts may be thin-walled tubular members having a plurality of slots disposed substantially parallel to the longitudinal axis of the tubular members, and adjacent grafts are flexibly connected by at least one connector member.

SUMMARY OF THE INVENTION

The present invention provides and improved method for implanting a coiled vascular ring prosthesis within a body passageway having a longitudinally extending central axis.

The method first places a coiled prosthesis upon a catheter in a coiled, smaller diameter configuration.

The prosthesis and catheter are inserted into the body passageway by catheterization of the body passageway.

The prosthesis is expanded in order to unwind the coiled prosthesis to a larger diameter configuration that has a diameter larger than the smaller diameter configuration of the prosthesis initially.

The prosthesis forms an annular ring having spaced apart first and second annular surfaces. The length of the ring between first and second annular surfaces can be very small in relation to the overall largest diameter of the ring. This feature allows the ring to be placed adjacent branches of vessels, and in curves as well as adjacent blockages that are very small.

The body passageway is supported in a direction away from the annular ring and along the passageway wall with multiple, longitudinally extending strut support members that each extend away from the ring, and each of which extends partially circumferentially around the passageway.

After the prosthesis has been expanded, the catheter is withdrawn from the body passageway.

In the preferred embodiment, the support members are spaced circumferentially about the ring.

In the preferred embodiment, the coiled prosthesis is uncoiled by inflating a balloon.

In the preferred embodiment, the prosthesis is a coiled ring member having a first predetermined collapsed smaller diameter, a central opening, and an inflatable balloon that occupies the central opening during insertion.

In the preferred embodiment, the prosthesis is metallic or plastic.

In the preferred embodiment, the prosthesis can be coated or impregnated with medication such as heparin, for example.

In the preferred embodiment, the catheter carries an inflatable balloon that uncoils the prosthesis and further comprising the step of locking the ring into the second maximum diameter to prevent a return to a coiled position with a diameter smaller than the second maximum diameter.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIGS. 4A and 4B are perspective and sectional views respectively illustrating damage to artery walls that can be caused by balloon angioplasty;

FIG. 5 is a perspective schematic view illustrating the method of the present invention during insertion of the guide wire into the damaged artery;

FIG. 6 is a sectional view of the method of the present invention illustrating insertion of the guide wire into the damaged artery;

FIG. 7 illustrates the method of the present invention prior to expansion of the coiled ring member;

FIG. 8 is a sectional view illustrating the method of the present invention prior to expansion of the coiled ring member;

FIG. 14 is a plan view of the coiled ring portion of the present invention shown in expanded flattened condition to illustrate the annular ring, strut portions, and locking device;

FIG. 15 is a sectional view taken along lines 15—15 of FIG. 14;

FIG. 16 is a sectional view taken along lines 16—16 of FIG. 14; and

FIG. 17 is a plan view of a second embodiment of the coiled ring portion of the present invention shown in flatened condition to illustrate ring, strut portions, and locking device.

Figure 1A:
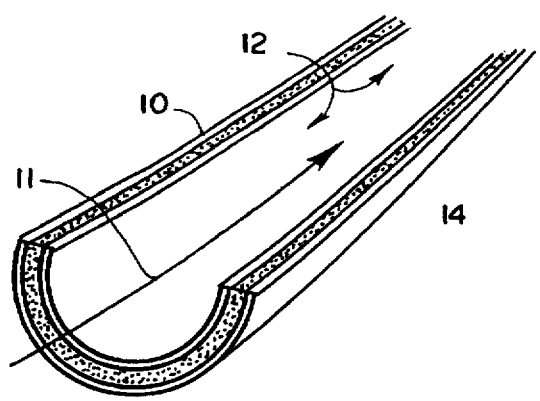
FIGS. 1A and 1B are perspective and sectional schematic views respectively illustrating a normal coronary artery with unrestricted blood flow.
Figure 1B:
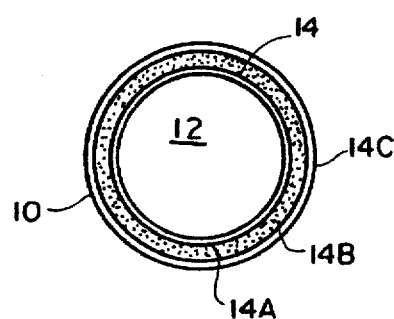

DETAILED DESCRIPTION OF THE PREFERRED EMBODIMENT:

FIGS. 1A-1B illustrate a normal coronary artery designated by the numeral 10 having unrestricted blood flow designated schematically by arrow 11 in FIG. 1A. Healthy coronary artery 10 has a wall 14 comprised of an inner layer 14A (intima), a media layer of thick muscular tissue 14B, and an outer layer (adventitia) 14C. Otherwise, the lumen 12 of healthy artery 10 is unrestricted and open for blood flow as defined by the inner layer 14A.

Figure 2A:
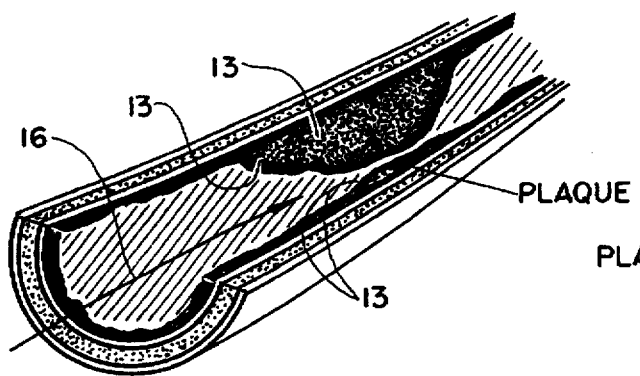
FIGS. 2A and 2B are perspective and sectional views respectively illustrating a diseased coronary artery with heavy plaque buildup and restricted blood flow.
Figure 2B:
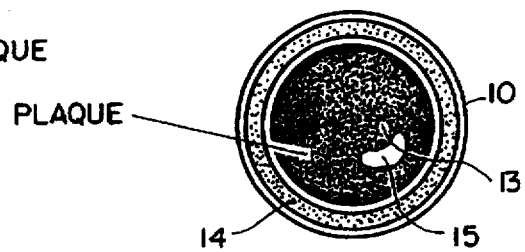

In FIGS. 2A-2B, a coronary artery 10 is illustrated that has become diseased with heavy plaque 13 buildup and having restricted blood flow through the restricted lumen 15. Arrow 16 designates restricted blood flow which must pass through the very small restricted lumen 15 that has become a restriction for blood flow because of the buildup of heavy plaque 13 occupying the majority of the normal dimensions of lumen 12.

Figure 3A:
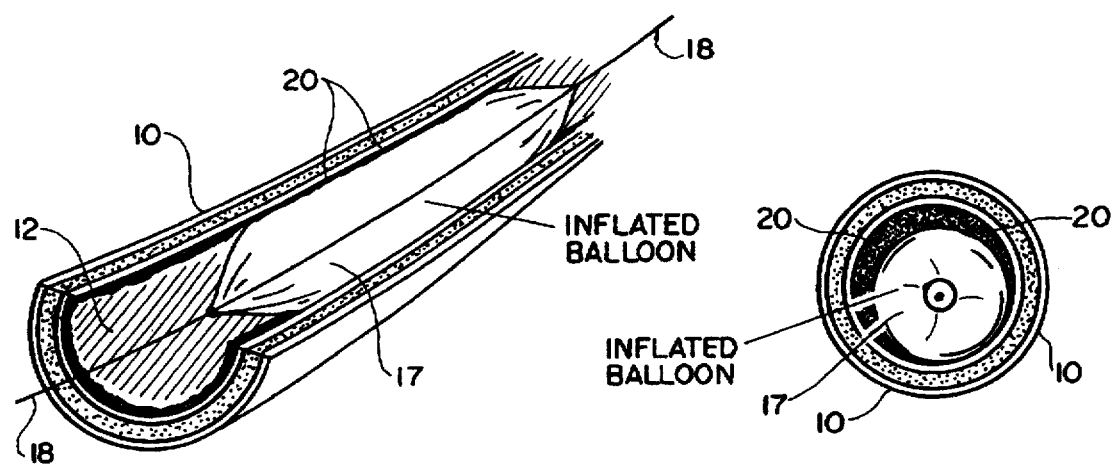
FIGS. 3A and 3B are perspective and sectional views respectively illustrating typical balloon angioplasty being used to compress plaque inside a patient's artery.
Figure 3B:
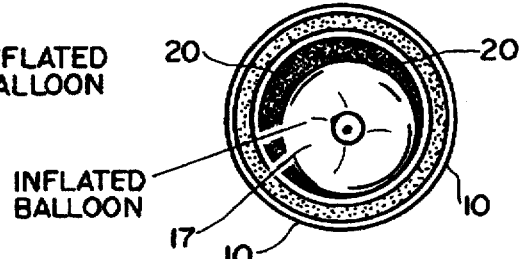

In FIGS. 3A-3B, a typical balloon angioplasty is used in the prior art is shown which as been used to compress the plaque inside the artery. Balloon 17 is placed in lumen 12 with a coronary guide wire 18 as is known in the art. Balloon 17 is initially deflated during catheterization of artery 10. However, when the obstruction and restricted lumen 15 is reached, balloon 17 is inflated and plaque buildup 13 compressed. In FIGS. 3A–3B, compressed plaque is designated generally by the numeral 20.

One of the problems with balloon angioplasty as illustrated in FIGS. 3A and 3B, is that the balloon angioplasty can sometimes damage artery wall 14. In FIG. 4A, guide wire 18 has been used to place balloon 17 adjacent an area of plaque buildup, designated as 20 in FIG. 4A. In FIG. 4A, balloon 17 has been deflated following expansion of the balloon used to compress plaque inside artery 10. However, the inflated balloon 17 has damaged a portion of the artery wall, the damaged area indicated as 21. In FIG. 4B, the damaged area 21 is illustrated more particularly showing the torn inner layer 14A and damaged media layer 14B.

FIG. 5A shows a perspective view of artery 10 and damaged area 21 of artery wall 14. A guide wire 22 has been placed in the lumen 12 of artery 10. After the guide wire is placed, according to the method of the present invention, a deflated balloon 23 carrying coiled ring structure 24 is inserted into the lumen 12 of artery 10. Ring 24 is coiled tightly around deflated balloon 13 so that the initial diameter of ring 24 is a smallest diameter which allows catheterization of artery 10 using wire 22 to carry deflated balloon 23 and coiled ring 24 into position adjacent damaged area 21.

Figure 9A:
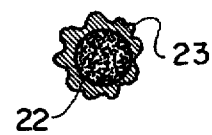
FIGS. 9A-9C are sectional schematic views illustrating expansion of the balloon and coronary ring members between an initial smaller diameter and a final larger diameter.

FIGS. 8 and 9A illustrate in section, the placement of guide wire 22, deflated balloon 23, and ring structure 24 in an initial position during catheterization and prior to inflation of balloon 23.

Figure 9B:
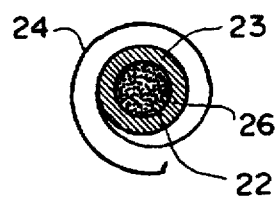
Figure 11:
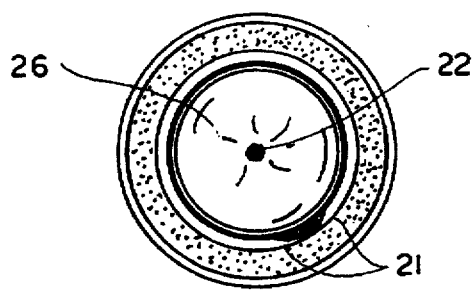
FIG. 11 is a sectional view of the preferred method of the present invention after inflation of the balloon and the coiled ring locked in place.
Figure 9C:
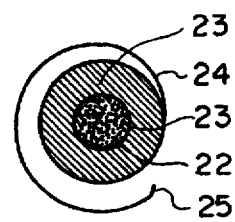
Figure 12:
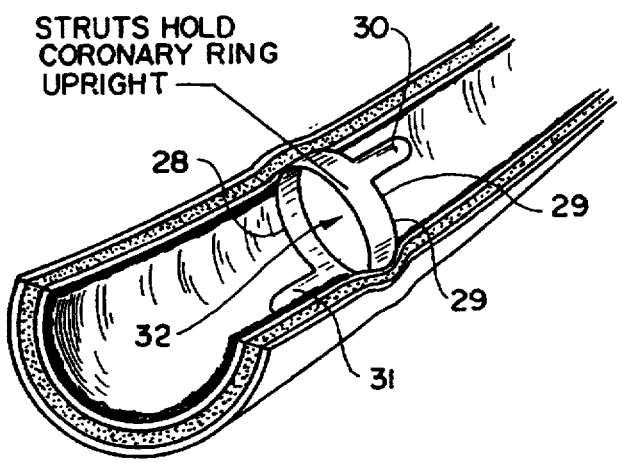
FIG. 12 is a perspective view illustrating the method of the present invention after the balloon is deflated and removed and the coiled ring has been positioned inside the patient's artery and locked in full open largest diameter position.
Figure 13:
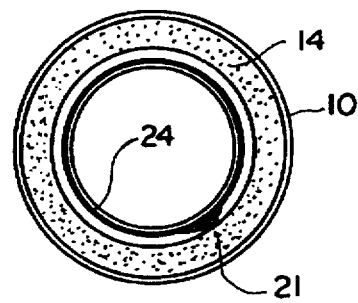
FIG. 13 is a sectional view illustrating the method of the present invention after the balloon is deflated and removed and the coiled ring has been positioned inside the patient's artery and locked in full open largest diameter position.

In FIGS. 9A–9C, sequential views respectively illustrate guide wire 22 prior to the inflation of balloon 23, in FIG. 9B, balloon 23 beginning to inflate, and in FIG. 9C, balloon 23 has been further inflated so that coronary ring 24 expands toward a maximum diameter.

Figure 10:
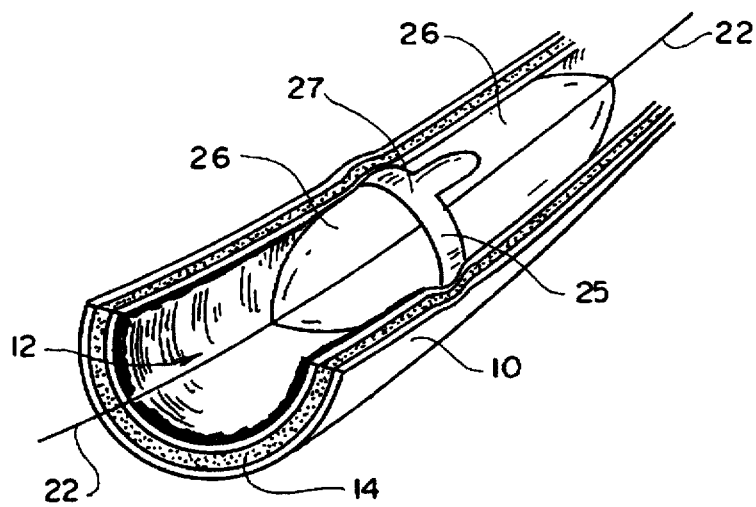
FIG. 10 is a perspective schematic view of the preferred method of the present invention after inflation of the balloon and the coiled ring locked in place.

In FIG. 10, the ring structure 25 can be seen as comprising an annular ring portion 27 having a pair of annular edges 28, 29. The length of the annular ring portion as measured from annular edge 28 to annular edge 29 is much smaller than the largest diameter of the ring portion 27 upon full expansion. For example the length can be one millimeter for a ring 27 with a 3 mm diameter upon expansion. This allows the ring structure 25 to be placed adjacent branch lines of an artery, and in restricted spaces, and in curved portions of arteries.

A longitudinally extending strut 30 extends longitudinally, generally parallel to the central longitudinal axis of bore 12. Similarly, strut 31 extends from annular surface 28 and away from ring structure 27, the strut 31 also extending generally parallel to the central longitudinal axis of lumen 12. In FIG. 10, wire 22 basically defines the central longitudinal axis of lumen 12 once balloon 26 is inflated. Central opening 32 in ring structure 27 allows unrestricted blood flow through ring structure 24. Struts 30, 31 extend longitudinally and in opposite directions from ring 27. Further, each strut tracks the inner layer 14A of artery wall 14 when ring structure 24 has been fully expanded. Thus, the struts 30, 31 function to hold the ring 27 upright, preventing its rotation or tipping with respect to the central longitudinal axis of lumen 12.

In FIG. 14, an enlarged view of ring structure 24 illustrates the ring if laid out flat, rather than in the coiled position. Ring structure 24 includes the annular ring 27 portion having a first end 33 and a second end 34. The end portion 33 provides a pointed member 34 that is bent inwardly as shown in FIG. 8 so that as the annular ring 27 expands, the pointed tip 35 registers with slot 36 of locking tab 37. The locking tab 37 includes side portions 38, 39. Slot 36 extends transversely across locking tab 37, terminating at end portions 40, 41 which provide a lateral dimension to slot 36 that is slightly smaller than the width of tab 37 between its edge portions 38, 39.

In FIG. 16, a strut 30 is shown in section, as including a raised portion 42 that can extend the full length of strut 30 between its point of attachment 43 to ring 27 and end portion 44 of strut 30. Raised portion 42 provides an increased cross section and thus a reinforcement to strut 30. Depending upon the length of strut 30 or 31, the configuration of raised portion 42 could be varied to provide sufficient strength so that struts 30, 31 do not unduly collapse or bend during use.

In FIG. 17, a second embodiment of the ring structure is illustrated, designated generally by the numeral 45. In the embodiment of FIG. 17, the ring structure provides a plurality of slots 46–48 so that the ring diameter can be adjusted to ever larger diameters as the balloon expands the annular ring 49 portion of the ring structure 45. The annular ring portion 49 provides end portions 50, 51 with the plurality of slots being carried by end portion 50, as shown in FIG. 17. The end portion 51 carries a pointed tip portion 52 that registers with each adjustable slot 46–48 as the balloon expands. This allows the cardiologist or technician to expand the ring 49 into an initial first diameter and then increase that diameter if desired. This also allows the ring to be expanded to larger diameters in subsequent procedures such as when blockage returns.

Each of the longitudinally extending struts 53, 54 carries a reinforcement 55, 56 respectively for preventing excessive bending of the struts during use.

As an example, the ring 49 could be adjusted to a first opened position of about 2.0 mm corresponding to a placement of the pointed tip 52 in the first slot 46. Further, the second slot 47 would represent a diameter of 2.5 mm for the annular ring 49. The slot 48 represents an adjustment position for a diameter of 3.0 mm. These dimensions could be provided for a first smaller ring, adjusted to the above-referenced positions as desired. However, a larger ring having adjustment positions of 3.5 mm, 4.0 mm, and 4.5 mm could also be provided so that a user achieves a broad range of ring 49 maximum diameters by providing the multiple slots 46–48 on each ring and by providing numerous rings of ever increasing maximum diameter.

The following Table 1 lists the part numbers and corresponding part descriptions as used herein in the written specification and the numbers as used in the attached drawing figures.

TABLE 1

PARTS LIST

| Part Number | Description |
| --- | --- |
| 10 | coronary artery |
| 11 | arrow |
| 12 | lumen |
| 13 | plaque |
| 14 | wall |
| 14A | inner layer |
| 14B | media layer |
| 14C | outer layer |
| 15 | restricted lumen |
| 16 | arrow |
| 17 | balloon |

TABLE 1-continued

PARTS LIST

| Part Number | Description |
|---|---|
| 18 | guide wire |
| 19 | compressed plaque |
| 20 | plaque buildup area |
| 21 | damaged area |
| 22 | guide wire |
| 23 | collapsed balloon |
| 24 | ring structure |
| 25 | locking end portion |
| 26 | inflated balloon |
| 27 | annular ring |
| 28 | annular edge |
| 29 | annular edge |
| 30 | strut |
| 31 | strut |
| 32 | opening |
| 33 | end portion |
| 34 | end portion |
| 35 | pointed tip portion |
| 36 | slot |
| 37 | locking tab |
| 38 | edge |
| 39 | edge |
| 40 | end portion of slot |
| 41 | end portion of slot |
| 42 | raised portion |
| 43 | attachment |
| 44 | end portion |
| 45 | ring |
| 46 | slot |
| 47 | slot |
| 48 | slot |
| 49 | annular ring |
| 50 | end |
| 51 | end |
| 52 | pointed tip |
| 53 | strut |
| 54 | strut |
| 55 | reinforcement |
| 56 | reinforcement |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A method for implanting a coiled prosthesis within a body passageway having a longitudinally extending central axis comprising the steps of:
   a) disposing a coiled prosthesis upon a catheter in a coiled small diameter configuration;
   b) inserting the prosthesis and catheter within the body passageway by catheterization of the body passageway;
   c) expanding the prosthesis to unwind the coiled prosthesis to a larger diameter configuration that has a diameter larger than the small diameter configuration of step "a";
   d) forming an annular ring with the prosthesis, having spaced apart first and second annular surfaces, wherein the length of the ring between annular surfaces is smaller than the diameter of the ring upon expansion, and said prosthesis having multiple, circumferentially spaced support members which extend longitudinally from each annular surface, each support member extending circumferentially only a partial distance around the circumference of the ring; and
   e) withdrawing the catheter from the body passageway after the prosthesis has been expanded.

2. The method of claim 1 wherein in step "c" the coiled prosthesis is uncoiled by inflating a balloon.

3. The method of claim 1 wherein the catheter carries an inflatable balloon that uncoils the prosthesis and further comprising the step of locking the ring into the larger diameter configuration to prevent a return to a coiled position with a diameter smaller than the larger diameter configuration.

4. An expandable intraluminal vascular coronary graft apparatus comprising:
   a) catheterization means for catheterizing a patient so that a blocked coronary artery can be accessed using a catheter;
   b) expandable coiled ring means for dilating the artery at the blockage site;
   c) means for expanding the ring means from a first small diameter to a second larger diameter;
   d) the ring means comprising a coiled ring that defines a fixed annular ring structure upon expansion to a second larger diameter, the ring having a length that is smaller than the diameter of the ring upon expansion; and
   e) multiple, circumferentially spaced and longitudinally extending support members, each extending from the ring longitudinally beyond one or more of its ends and extending circumferentially only a partial distance along the artery wall.

5. The graft of claim 4 wherein the ring carries medication.

6. The apparatus of claim 4 wherein in part "b" the coiled ring means is a coiled ring member having a first predetermined collapsed small diameter and a central opening, and in part "c" the means for expanding comprises an inflatable balloon that occupies the central opening during insertion.

7. The apparatus of claim 4 wherein the ring means is metallic.

8. The apparatus of claim 4 wherein the ring means is plastic.

* * * * *